United States Patent [19]

Paust et al.

[11] 4,359,582
[45] Nov. 16, 1982

[54] EXTRACTION OF PANTOLACTONE FROM ITS AQUEOUS SOLUTIONS

[75] Inventors: Joachim Paust, Neuhofen; Wolfram Schmidt, Friedelsheim, both of Fed. Rep. of Germany

[73] Assignee: BASF Aktiengesellschaft, Fed. Rep. of Germany

[21] Appl. No.: 10,726

[22] Filed: Feb. 8, 1979

[30] Foreign Application Priority Data

Mar. 3, 1978 [DE]  Fed. Rep. of Germany ....... 2809179

[51] Int. Cl.$^3$ ............................................ C07D 307/20
[52] U.S. Cl. ................................................... 549/319
[58] Field of Search ...................... 260/343.6; 549/319

[56] References Cited

U.S. PATENT DOCUMENTS 3,996,246  12/1976  Hoffmann et al. .............. 260/343.6

FOREIGN PATENT DOCUMENTS 1568755  3/1972  Fed. Rep. of Germany ... 260/343.6
2228641  4/1973  Fed. Rep. of Germany ... 260/343.6

*Primary Examiner*—Ethel G. Love
*Attorney, Agent, or Firm*—Keil & Witherspoon

[57] ABSTRACT

Pantolactone is extracted from its aqueous solutions using methyl tert.-butyl ether as the extractant.

1 Claim, No Drawings

EXTRACTION OF PANTOLACTONE FROM ITS AQUEOUS SOLUTIONS

The present invention relates to an improved process for the extraction of pantolactone from its aqueous solutions.

Pantolactone (ie. the lactone of 2,4-dihydroxy-3,3-dimethyl-butyric acid) is an intermediate in the preparation of pantothenic acid and related physiologically active compounds. Using the conventional industrial methods of synthesis, the product is obtained by hydrolysis of 2,4-dihydroxy-3,3-butyronitrile, in which case it arises in the form of acid aqueous solutions from which it has to be isolated. Extraction processes are used for this purpose, but the extractants used hitherto are not entirely satisfactory. It is true that the chlorohydrocarbons principally used for this purpose, eg. chloroform and methylene chloride (cf., for example, German Published Application DAS 2,228,641) are very suitable, if viewed solely from the extraction aspect, but because of their toxicity, they present environmental disadvantages when used for industrial syntheses. Because of their high vapor pressure, they are always carried in the off-gas, from which they can only be removed at great expense. Diethyl ether has also already been used as the extractant (German Published Application DAS 1,568,755) but because of the relatively low solubility of pantolactone therein, the amounts of extractant required are economically unacceptable. Diethyl ether is also rather unsuitable for industrial processes because it is significantly soluble in water and because, like most other ethers, it tends to form peroxides.

It is an object of the present invention to provide a more suitable extractant so that pantolactone can be isolated from its aqueous solutions by a method which overall is more economical.

We have found that this object is achieved and that pantolactone can be extracted successfully from its aqeuous solutions by means of an organic extractant if methyl-tert.-butyl ether (MTB) is used as the extractant.

From the point of view of the distribution ratio, MTB is as suitable as methylene chloride for extracting pantolactone from an aqueous phase, but it does not suffer from the disadvantages of the chlorohydrocarbon. The MTB entering the off-gas can be burnt harmlessly, while MTB in waste water is biodegradable. Furthermore, MTB does not form peroxides, and is readily obtainable from cheap starting materials, namely methanol and isobutene. Finally, MTB offers the technological advantage that the MTB phase is always substantially lighter than the aqueous phase and hence phase separation presents none of the difficulties encountered with methylene chloride, which is of about the same density as the aqueous phase.

The solutions to be extracted are in most cases acid aqueous solutions having an initial pantolactone content of from 6 to 20% by weight. Advantageously, from 0.5 to 2 kg of MTB are used per kilogram of such a solution, so as to achieve, at each extraction step, a depletion to about 20% of the original pantolactone concentration in the aqueous phase. The extraction can be carried out by all the conventional extraction techniques, ie. batchwise, in a cascade or completely continuously by the liquid-liquid countercurrent method, using packed columns or tray columns under atmospheric or slightly superatomspheric pressure, and preferably at from 20° to 40° C. The process according to the invention may be used both to isolate D,L-pantolactone from the aqueous mixture resulting from its synthesis, and for isolating the pure optical isomers after resolution of the racemate via pantoic acid salts and regeneration of the D-pantolactone or L-pantolactone; furthermore, the process may be used regardless of whether the aqueous solution also contains other materials, particularly salts, eg. ammonium sulfate or sodium sulfate. The presence of salts is even advantageous, because of the salting-out effect.

The working up of the MTB-pantolactone solutions also employs conventional methods, for example distillation or, in the case of substantially pure optical pantolactone isomers, preferably crystallization. For some purposes, the solutions obtained can also be used directly.

EXAMPLE

An aqueous solution originating from the synthesis of pantolactone and containing 22% (all percentages being by weight) of pantolactone, 3% of sulfuric acid, 11% of ammonium sulfate and 12% of sodium sulfate was stirred for 10 minutes at 25° C. with 0.6 kg of MTB per kilogram of solution, and after phase separation the MTB phase was worked up by distillation to recover the pantolactone.

90% of the pantolactone were obtained in this way; the remainder persisted in the aqueous phase, from which it was extracted virtually quantitatively in two subsequent steps each using 0.6 kg of MTB. The losses of MTB amounted to only 1% of the total amount employed.

We claim:

1. A process for the extraction of pantolactone from its aqueous solutions by means of an organic extractant, wherein methyl tert.-butyl ether is used as the extractant.

* * * * *